(12) United States Patent
Teasdale

(10) Patent No.: US 7,785,254 B2
(45) Date of Patent: Aug. 31, 2010

(54) SURGICAL TOOL HOLDER

(75) Inventor: Peter Teasdale, Sheffield (GB)

(73) Assignee: Automated Medical Products Corporation, Sewaren, NJ (US)

( * ) Notice: Subject to any disclaimer, the term of this patent is extended or adjusted under 35 U.S.C. 154(b) by 564 days.

(21) Appl. No.: 11/166,199

(22) Filed: Jun. 27, 2005

(65) Prior Publication Data

US 2006/0293569 A1 Dec. 28, 2006

(51) Int. Cl.
*A61B 1/32* (2006.01)
(52) U.S. Cl. .................. 600/228; 600/226; 600/227; 600/229; 600/230; 600/231; 600/232; 600/233; 600/234
(58) Field of Classification Search .......... 600/226–234
See application file for complete search history.

(56) References Cited

U.S. PATENT DOCUMENTS

| | | | | |
|---|---|---|---|---|
| 3,129,706 A | * | 4/1964 | Reynolds, Jr. ............... | 600/233 |
| 3,227,156 A | * | 1/1966 | Gauthier ..................... | 600/231 |
| 4,143,652 A | | 3/1979 | Meier et al. ................. | 128/20 |
| 4,852,552 A | * | 8/1989 | Chaux ........................ | 600/232 |
| 4,945,897 A | * | 8/1990 | Greenstein et al. .......... | 600/210 |
| 5,167,223 A | * | 12/1992 | Koros et al. ................. | 600/232 |
| 5,365,921 A | * | 11/1994 | Bookwalter et al. ......... | 600/232 |
| 5,772,583 A | * | 6/1998 | Wright et al. ............... | 600/232 |
| 5,902,233 A | * | 5/1999 | Farley et al. ................ | 600/213 |
| 6,302,843 B1 | * | 10/2001 | Lees et al. .................. | 600/228 |

FOREIGN PATENT DOCUMENTS

WO PCT/US00/04696 9/2000

* cited by examiner

*Primary Examiner*—Thomas C Barrett
*Assistant Examiner*—Sameh Boles
(74) *Attorney, Agent, or Firm*—Dorsey & Whitney LLP

(57) ABSTRACT

A surgical tool holder that includes a base portion, an incremental retraction portion, and an attachment portion. The base portion is configured for releasably mounting to a first surgical tool support in a fixed association. The incremental retraction portion includes a drawing mechanism configured for operably engaging and incrementally drawing a surgical retractor under tension to a selected position and holding the surgical retractor in the selected position, and a crank member configured to operate the drawing mechanism. The attachment portion includes a post configured for rotatably mounting a yoke of a second surgical tool support, and a securing member operably associated with the post for releasably fixing the second surgical tool support thereto.

22 Claims, 8 Drawing Sheets

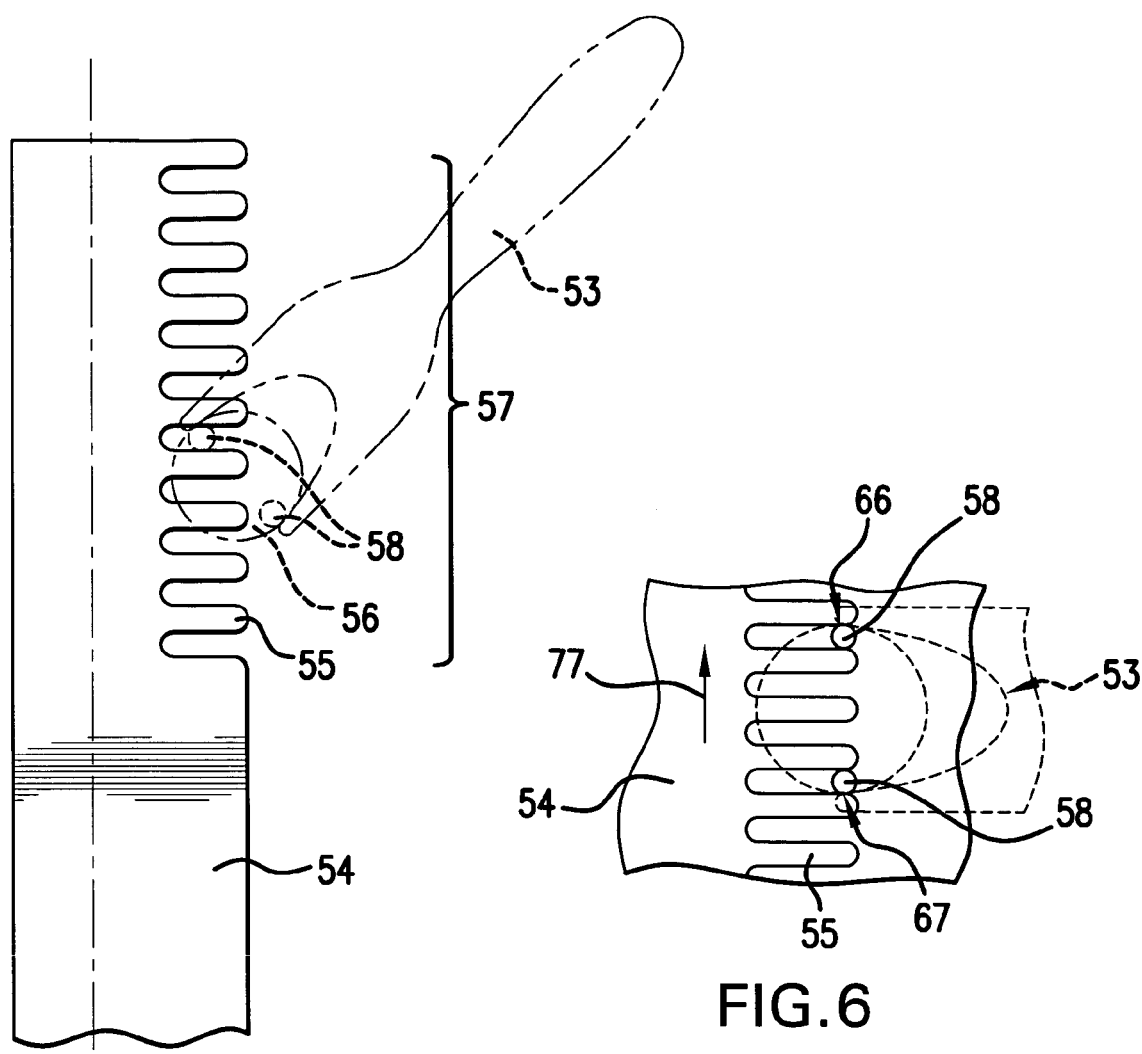
FIG.5
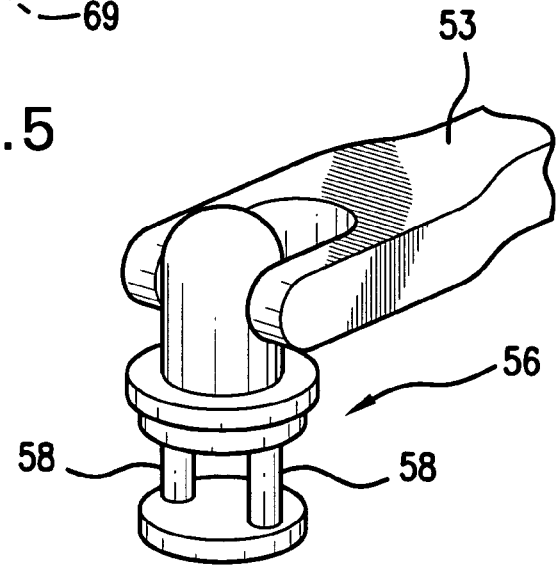
FIG.7

SURGICAL TOOL HOLDER

FIELD OF THE INVENTION

The present invention relates generally to a surgical tool holder for use during surgical procedures. More particularly, the invention relates to a surgical tool holder for supporting a surgical retractor.

BACKGROUND OF THE INVENTION

Surgical tool holders are used to securely and stably maintain tools in a fixed position so that a physician or physician's assistant does not have to manually hold the tools throughout the duration of the surgical procedure. Some known surgical tool holders are designed to be removably mounted or otherwise attached to a surgical tool support or a horizontal bar, which is positioned over the patient and further connects to the surgical tool support, that is fixed to the operating room table. An example of a surgical tool support is described in U.S. Pat. No. 4,143,652, the content of which is hereby incorporated herein by reference thereto, or a surgical tool support of the system sold under the trademark Iron Intern® by Automated Medical Products Corp.

Tools that are commonly held by such surgical tool holders include, for example, retractors for retracting internal organs, and other structures, such as a patient's ribcage. The Stieber Rib Grip Kit® sold by Automated Medical Products Corp. is used, for instance, for retracting the ribs during abdominal surgery to retract the upper middle abdomen of a patient.

U.S. Pat. No. 6,302,843 describes a tool holder platform that can be mounted to horizontal bar that is positioned above a patient to hold a hydra, which, with various support arms, supports other tools such as a retractor to retract and maintain organs in the retracted position.

It is desirable to reduce the number of tool holders and supports that are used during a surgical procedure to decrease the amount of equipment that needs to be assembled and sterilized and also to increase the amount of room around the patient within which the physician can operate.

Thus, there is a need for a simple surgical tool holder that can hold a combination of various types of retractors as well as incrementally draw a retractor, such as for a ribcage.

SUMMARY OF THE INVENTION

The present invention relates to a surgical tool holder used during surgical procedures and a method of preparing thereof. The preferred embodiment includes a base portion configured for releasably mounting to a first surgical tool support in a fixed association and an incremental retraction portion. The retraction portion includes a drawing mechanism configured to operably engage and incrementally draw a surgical retractor under tension to a selected position and hold the surgical retractor in the selected position, and a manually operable crank member configured to operate the drawing mechanism. The preferred embodiment also includes an attachment portion comprising a post configured to rotatably mount a yoke of a second surgical tool support, and a securing member operably associated with the post to releasably fix the second surgical tool support thereto.

Preferably, the base portion is configured to releasably mount to a cylindrical bar of the first surgical tool support. More preferably, the base portion comprises a clamping member defining a bore configured and dimensioned to receive, and clamp to, the cylindrical bar. The bore preferably has a bore axis, and the incremental retraction portion and the attachment portion are disposed substantially on opposite sides of the bore axis.

The incremental retraction portion preferably includes a drawing housing configured to receive and guide the surgical retractor during retraction. Preferably, at least a portion of the clamping member is of unitary construction with at least a portion of the drawing housing. Preferably, the drawing mechanism and crank member are rotatable to incrementally draw the surgical retractor. Preferably, the drawing mechanism includes a pinion operably engageable with a rack of the surgical retractor. In another embodiment, the drawing mechanism also preferably includes a ratchet.

Preferably, the incremental retraction portion is configured to draw the surgical retractor in a drawing axis, and the post has a post axis that extends from about 60° to 120° from the drawing axis. The incremental retraction portion is also preferably configured to draw the retractor along a substantially nonadjustable drawing axis that is oriented about 60° to 120° from the bore axis. Preferably, the bore has a bore diameter, and the incremental retraction portion is oriented to draw the surgical retractor aligned within the bore diameter outside the bore. More preferably, the incremental retraction portion is oriented to draw the surgical retractor within half of one bore diameter outside the bore.

The attachment portion preferably includes a platform supportively connecting the post to the base portion, and the post extends from the platform substantially tangentially to the bore axis. The attachment portion also preferably includes a locating protrusion disposed for positioning the yoke axially on the post, and the securing member is operably associated with the post to clamp the post-mounted yoke against the locating protrusion. Preferably, the securing member is in threaded association with the post to clamp against the yoke mounted thereon. More preferably, the securing member includes a wing nut.

In the preferred embodiment, the surgical retractor includes a rack configured and dimensioned to mesh with a pinion to draw the rack upon rotation of the pinion. The rack and pinion are configured such that the pinion is rotatable to at least one blocking position in which the pinion blocks further extension of the rack from the selected position in a direction opposite from which it is drawn by the incremental retraction portion. Preferably, the pinion is configured to draw the rack in a drawing axis and has proximal and distal sides aligned parallel to the drawing axis, and the rack includes teeth that are engaged with the pinion extending to the proximal and distal sides to provide the at least one blocking position.

The base portion can be fixed with the first surgical tool support with the surgical retractor in drawn association with the incremental retraction portion. The second surgical tool support can include a hydra, secure and fixed on the post. Preferably, the surgical tool holder is positioned to, and the surgical retractor is configured to, retract the patient's xiphoid. More preferably, the surgical retractor comprises a curved retraction blade having a notch configured and disposed to receive the tip of the xiphoid to minimize or prevent damage thereto during the retraction thereof.

The invention thus provides a surgical tool holder that can securely and stably maintain in a fixed position both a surgical retractor, which can be incrementally drawn to incrementally retract a portion of the patient's body, and another surgical tool support.

BRIEF DESCRIPTION OF THE DRAWINGS

FIG. 5 is a front view showing the association between the rack of the surgical retractor and the pinion of the drawing mechanism of the embodiment of FIG. 1;
FIG. 6 is a cut-away view thereof in a blocking position;
FIG. 7 is a perspective view of the rack and crank member thereof.

DETAILED DESCRIPTION OF THE PREFERRED EMBODIMENTS

Figure 1:
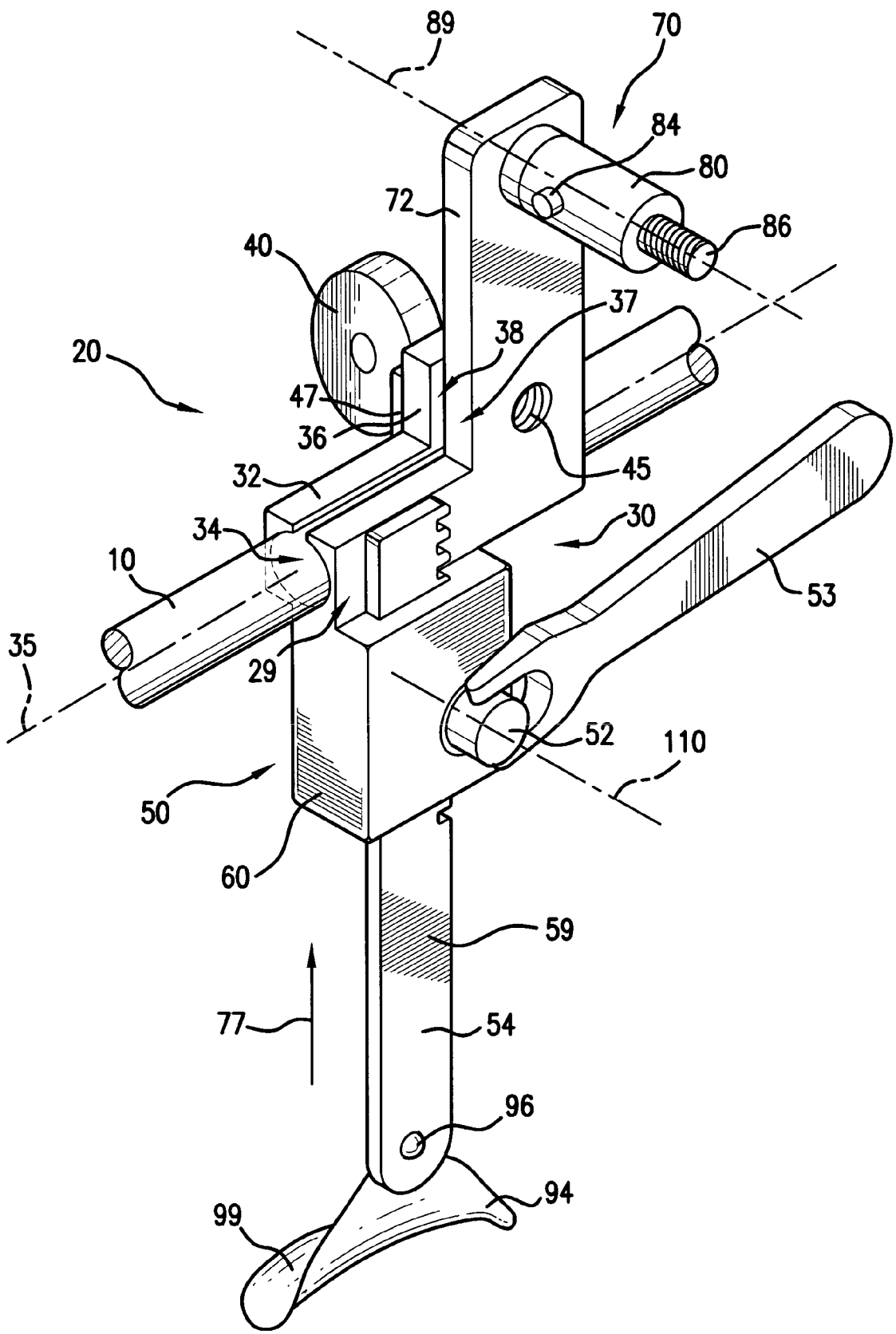
FIG. 1 is a perspective view of an embodiment of the surgical tool holder constructed according to the present invention.

FIG. 1 shows a preferred embodiment of a surgical tool holder 20 that includes a base portion 30, an incremental retraction portion 50, and an attachment portion 70. Preferably, the tool holder 20 is made of a unitary material, such as of surgical grade stainless steel, that is either milled, forged, or machined. Alternatively, the tool holder 20 can be made of separate pieces that are preferably integrally joined, such as by welding, adhering, riveting, or otherwise fastening.

The base portion 30 is preferably configured for separably and releasably mounting or attaching to a surgical tool support in a fixed association therewith. By mounting to a surgical tool support, the tool holder 20 can stably hold and maintain surgical tools, such as retractors, in a retracted position as long as desired throughout the duration of a surgical procedure.

Figure 10:
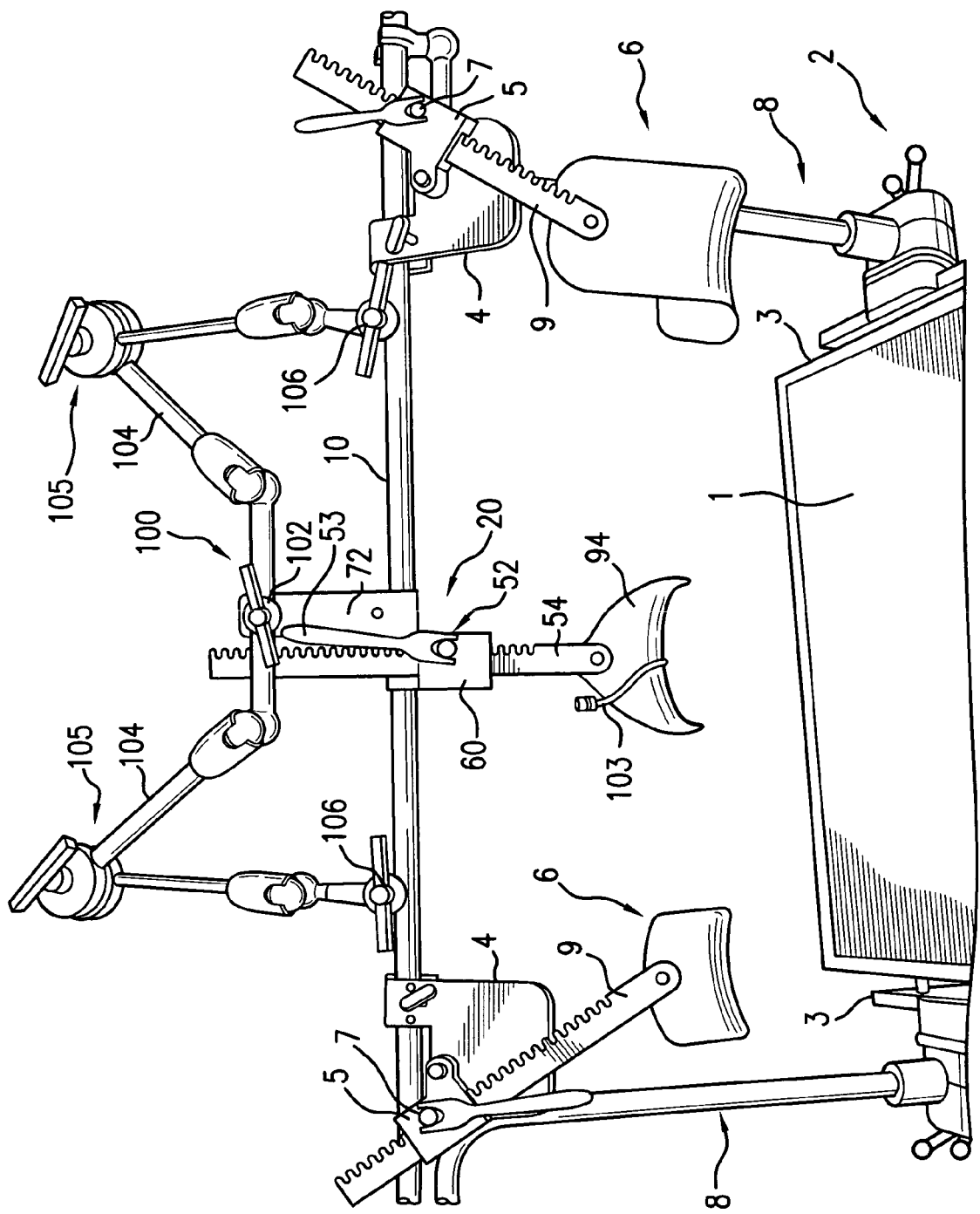
FIG. 10 is a perspective view of another embodiment of an assembly using the tool holder of FIG. 1.

Preferably, the base portion 30 is separably and releasably mounted to the surgical tool support by using a clamp or other securing device. In the preferred embodiment shown in FIG. 1, the base portion 30 is configured for separably and releasably mounting to a cylindrical bar 10 of a surgical tool support, such as the one described in U.S. Pat. No. 4,143,652. As shown in FIG. 10, the surgical tool support 8 is preferably fixed or secured to the operating room table 1 such that it extends substantially upwardly, and can extend substantially vertically, therefrom, and the cylindrical bar 10 can extend substantially horizontally from the surgical tool support 8 such that the bar 10 is positioned over the patient when lying on the operating table 1. With the cylindrical bar 10 positioned in this manner, the base portion 30 of the tool holder 20 can be separably and releasably mounted thereto.

Referring to FIGS. 1-4, the preferred embodiment of the base portion 30 includes a clamping member 32 that defines a bore 34 that is configured and dimensioned to receive and clamp to the cylindrical bar 10 of the surgical tool support. The clamping member 32 preferably has an axial length 31 along which the clamping member receives and clamps to the cylindrical bar 10. Preferably, the clamping member 32 has a minimum length 31 of at least about 20 mm and more preferably of at least about 40 mm. The maximum length 31 of the clamping member 32 is preferably about 120 mm and more preferably is about 100 mm. Preferably, the length 31 of the clamping member 32 is substantially equal to the length of the entire base portion 30 aligned with a bore axis 35. In the preferred embodiment, the length 31 is about 70 mm.

The bore 34 preferably runs through the entire clamping member 32 along the bore axis 35. Preferably, the bore 34 has a diameter 33 configured to receive the cylindrical bar 10. Preferably, the diameter 33 is at least about 7 mm and more preferably is at least about 10 mm. Also, the diameter 33 is preferably at most about 25 mm and more preferably is at most about 20 mm. In the preferred embodiment, the diameter 33 is about 15 mm.

Figure 2:
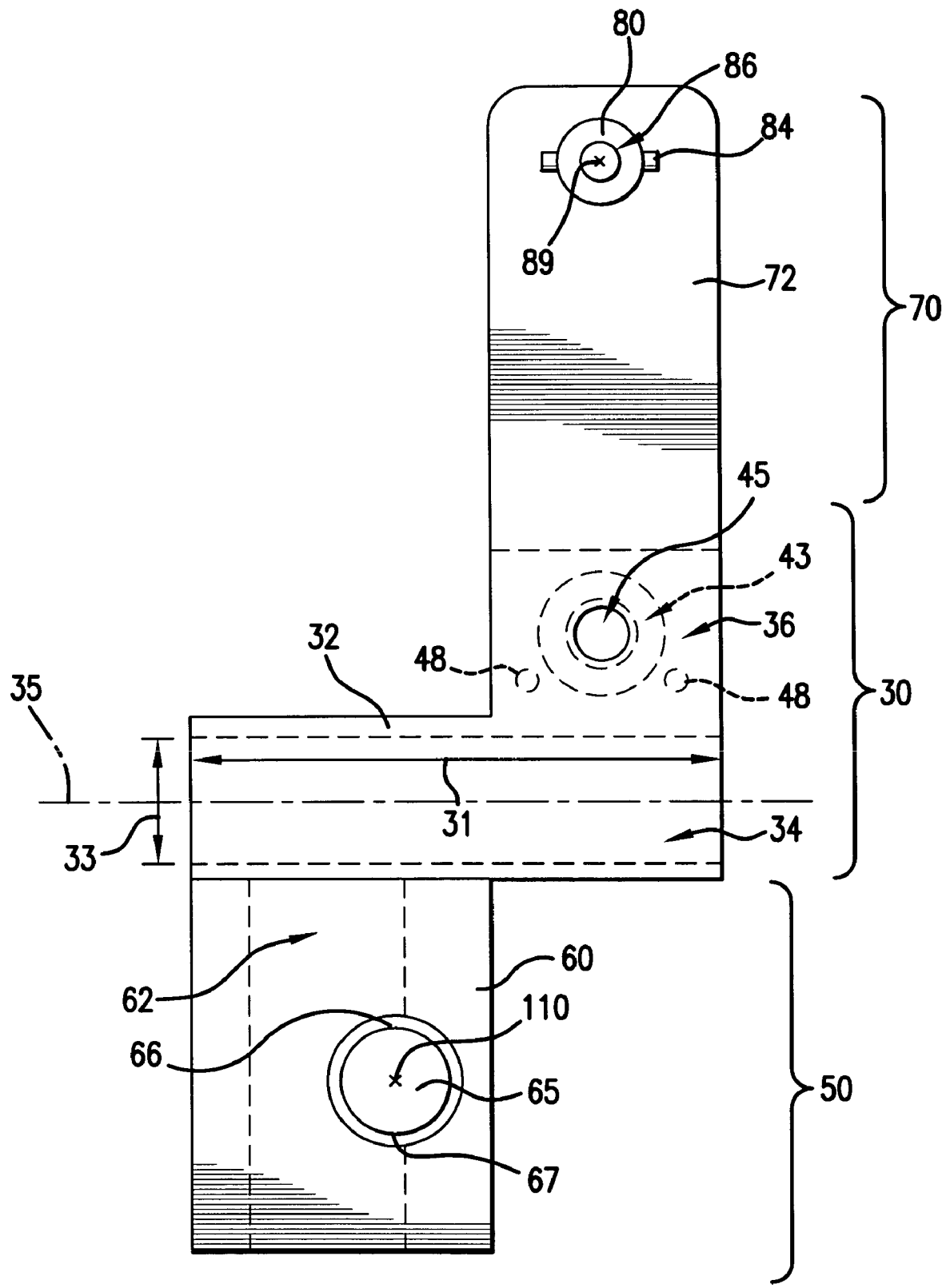
FIG. 2 is a front view of the main body thereof.
Figure 3:
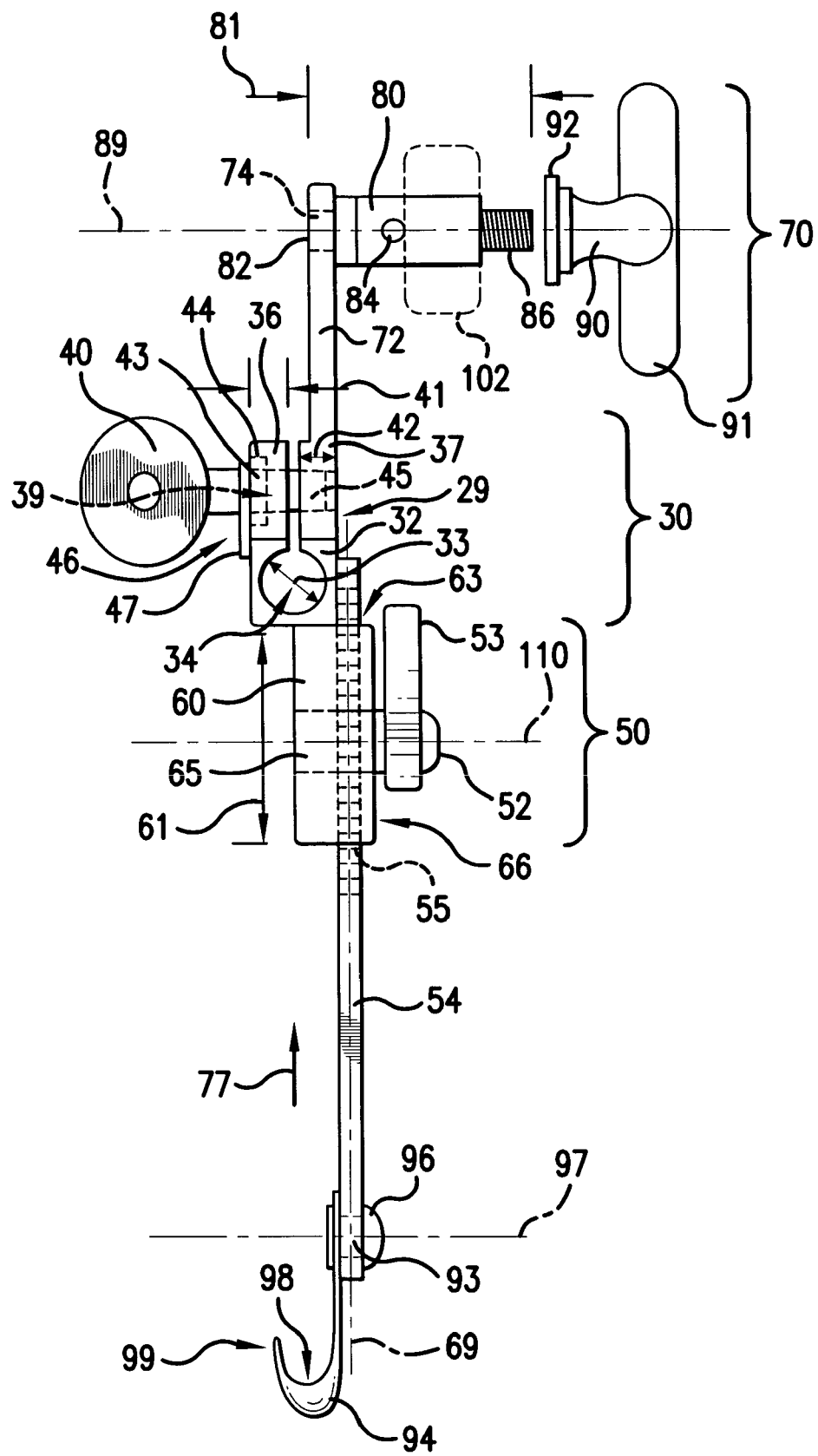
FIG. 3 is a side view of the assembly of FIG. 1.

Preferably, the clamping member 32 includes two clamping portions 36,37, shown in FIGS. 1 and 3, that define a slot 38 therebetween, and which are configured for tightening or loosening around the bar 10. Preferably, the slot 38 extends from the bore 34 to the top of the clamping portions 36,37 and is configured such that the clamping portions 36,37 can move relative to each other to either tighten or loosen the clamping member 32. Preferably, one of the clamping portions, for example clamping portion 36 as shown in FIG. 3, is a first clamping portion and the other clamping portion, for example clamping portion 37 as shown in FIG. 3, is a second clamping portion. In the preferred embodiment shown in FIGS. 1-4, the first clamping portion 37 is oriented on the backside of the tool holder 20 and the second clamping portion 37 is oriented on the front side of the tool holder 20.

Referring to FIG. 3, the first clamping portion 36 preferably includes a bore 39 that is configured and dimensioned for receiving a key 40 or other locking member therethrough. Preferably, the second clamping portion 37 also includes a bore 45 that is axially aligned with the bore 39 of the first clamping portion 36 and that is also configured and dimensioned for receiving the key 40 therethrough. Preferably, the bores 39,45 extend, respectively, through the entire thicknesses 41,42 of the first and second clamping portion 36,37, and the bore 45 and key 40 are in threaded association with each other. Preferably, the key 40 is of sufficient length such that the key 40 can extend through the slot 38 to be received and threaded in the bore 45 of the second clamping portion 37.

The first clamping portion 36 also preferably includes a recess 43 at the surface thereof opposite the slot 38. Preferably, the recess 43 has a diameter that is substantially greater than the diameter of the bore 39, and the recess 43 is configured and dimensioned for receiving with a flange 44 of the key 40. In this configuration, as the key 40 is threaded through the bore 45, the flange 44 contacts with the recess 43 to push the first clamping portion 36 in the direction of the second clamping portion 37, which in turn tightens the clamping member 32 around the cylindrical bar 10 to secure the tool holder 20 thereon.

Preferably, the first clamping portion 36 also includes a retaining mechanism 46, preferably associated with the key 40 and first clamping portion 36, to prevent the key 40 from being removed from threaded association with bore 45. In the preferred embodiment shown in FIG. 3, the fixing mechanism 46 includes a plate 47 that is attached to the surface of the first clamping portion 36 opposite the slot 38 to trap the flange 44 of the key 40 within the recess 43. Preferably, the plate 47 is attached to the surface of the first clamping portion 36 by fasteners 48. With the plate 47 attached in this manner, the key 40 is preferably prevented from being fully released and removed from threaded association with the bore 45, to advantageously prevent loss or misplacement of the key during assembly, disassembly, or sterilization of the tool holder 20.

In this configuration, the tool holder 20 of the preferred embodiment can be releasably clamped to a cylindrical bar 10 of a tool support above the patient for optimally positioning the tool holder 20 for retraction of organs or skeletal structures, such as the ribcage, and preferably the xiphoid of the patient. In other embodiments, the clamping member can include other mechanisms for tightening and loosening the clamping member around the bar.

The incremental retraction portion 50 is preferably configured for mounting or attaching a surgical retractor 54 to the tool holder 20, and more preferably for mounting a xiphoid retractor thereto. Preferably, the retraction portion 50 includes a housing 60 that is configured to receive and guide the surgical retractor 54 during retraction. The housing 60 extends from the base portion 30, preferably from the opposite side of the base portion 30 from which the attachment portion 70 extends, and more preferably from the bottom of the clamping member 32. In the preferred embodiment, at least a portion of the clamping member 32 is of unitary construction with at least a portion of the housing 60. The housing 60 preferably extends from the clamping member 32 at an axial length 61 of at least about 30 mm and more preferably of at least about 40 mm. The length 61 is also preferably at most about 80 mm and more preferably is at most about 60 mm. In the preferred embodiment, the axial length 61 of the housing 60 is about 50 mm.

Preferably, the housing 60 includes a slot 62 that extends longitudinally with respect to the length 61 of the housing 60, and which runs from the top 63 of the housing through to the bottom 64 of the housing to define a drawing axis 69. The slot 62 is configured and dimensioned to receive the surgical retractor 54 such that the surgical retractor 54 can be drawn therethrough in a drawing direction 77 along the drawing axis 69, which is preferably substantially straight and not repositionable or adjustable with respect to the bore axis 35. The drawing axis 69 is oriented with respect to the bore axis 35 at an angle that is preferably at least about 45° and more preferably is at least about 60°, and preferably is at most about 135° and more preferably is at most about 120°. In the preferred embodiment, the drawing axis 69 and the bore axis 35 are substantially orthogonal to each other. In another embodiment, the drawing axis can be adjustable with respect to the bore axis, but in the preferred embodiment, the drawing axis 69 is disposed to enable retraction of the xiphoid without requiring a physician to position it during the surgical procedure.

The width and depth of the slot 62 is preferably slightly larger than the width and depth of the surgical retractor 54. Preferably, the housing 60 and the slot 62 that runs therethrough are oriented with respect to the clamp member 32 such that the top 63 of the housing 60 and slot 62 is substantially orthogonal to the front face 29 of the clamp member 32, as shown in FIG. 3. In the preferred embodiment, the front face 29 is continuous with the back side of the slot 62. Preferably, the retraction portion 50 and the housing 60 are oriented with respect to the clamp member 32 to draw the surgical retractor 54 along the drawing axis 69 such that the retractor 54 is aligned within the distance of one bore diameter 33 outside the bore 34. Even more preferably, retractor 54 is aligned to be drawn within the distance of half of one bore diameter 33 outside the bore 34. In this configuration, the incremental drawing of the surgical retractor 54 through the slot 62 does not interfere with manipulation of the base portion 30 or the post 80 and the tool support 100 mounted thereto.

The retraction portion 50 also preferably includes a drawing mechanism 52 and a crank member 53, which is configured and dimensioned for operating the drawing mechanism 52. The drawing mechanism 52 is preferably configured for engaging and drawing, preferably incrementally, the surgical retractor 54 under tension to a selected position and holding and maintaining the surgical retractor 54 in that position. In this manner, the retraction blade 94 of the surgical retractor 54, such as for example a xiphoid retractor, can be positioned under the xiphoid, and the drawing mechanism 52 can incrementally and controllably draw or retract the surgical retractor 54 upward and maintain it in such a position so that surgical retractor 54 supports the xiphoid in the retracted position.

Figure 4:
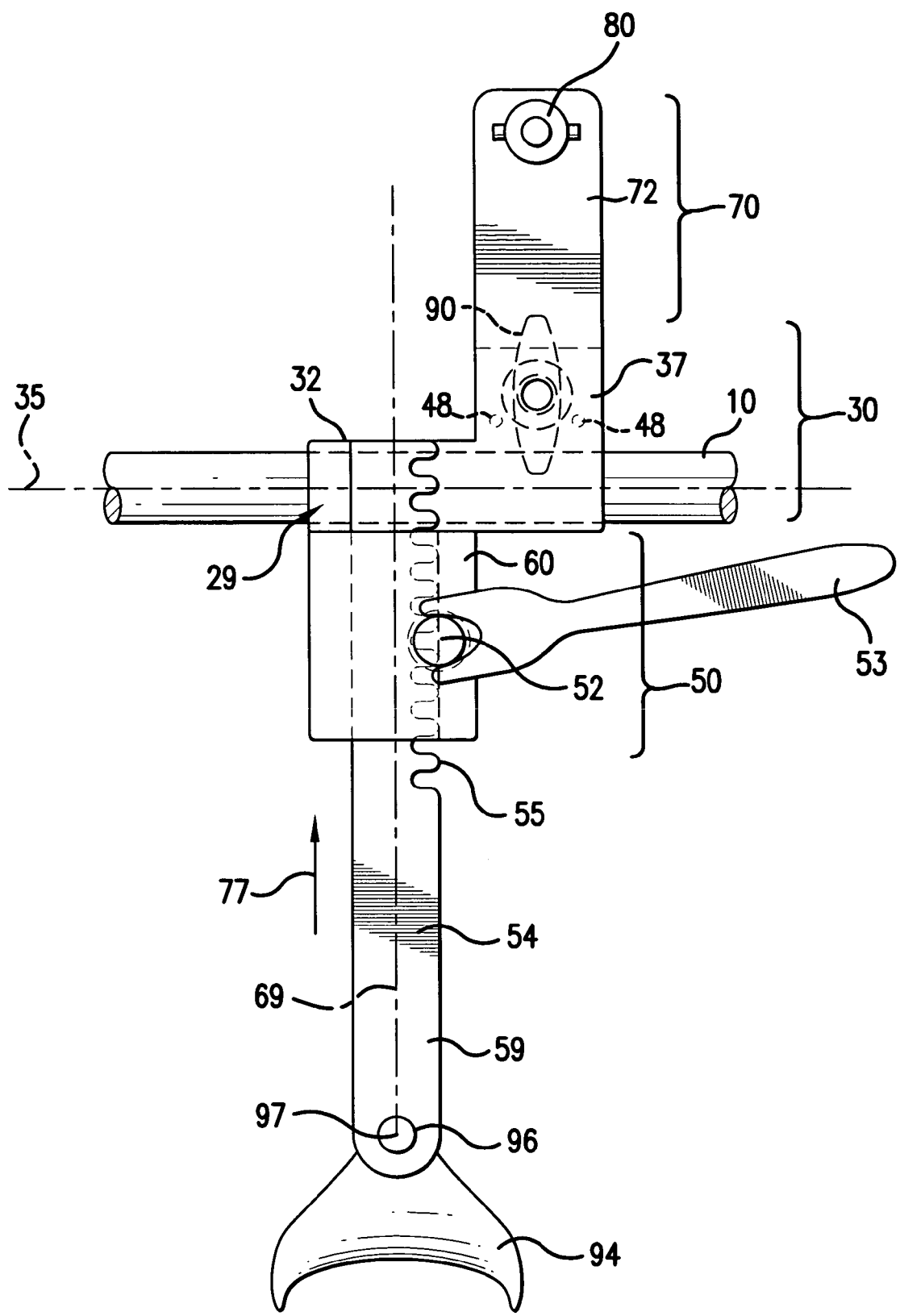
FIG. 4 is a front view thereof.

Preferably, the crank member 53 is configured for associating with the drawing mechanism 52 to draw the surgical retractor 54 through the slot 62. In the preferred embodiment, the crank member 53 is manually operated and as shown in FIGS. 1, 4 and 7, the crank member 53 is associated with the drawing mechanism 52 at a hinge such that the crank member 53 can pivot about the drawing mechanism 52, but is rotatably coupled therewith to rotate the drawing mechanism 52 to draw the surgical retractor 54 through the slot 62. In other embodiments, the crank member can be associated with the drawing mechanism in other configurations.

The housing 60 preferably includes a bore 65 located on the front face 68 of the housing 60, and which is configured and dimensioned for receiving and seating the drawing mechanism 52 therein for engagement with the surgical retractor 54 to draw the retractor through the slot 62. Preferably, the bore 65 extends through the entire depth of the housing 60 and bisects the slot 62, and more preferably orthogonally extends across the slot 62. In the preferred embodiment, the bore 65 is offset with respect to the slot 62 such that the bore 65 intersects only one side of the slot 62, as shown in FIG. 4. In this configuration, the drawing mechanism 52 can drawingly associate with teeth 55 that are disposed on one side of the retractor 54 to draw the retractor 54 through the slot 62.

The drawing mechanism 52 and the crank member 53 are preferably rotatable within the bore 65 to incrementally draw the surgical retractor 54 through the slot 62. Preferably, the drawing mechanism 52 includes a pinion 56 that is configured and dimensioned to engage and associate with a rack 57 that is defined by the teeth 55 of the surgical retractor 54. More preferably, the rack 57 is in meshable association with the pinion 56 such that as the pinion 56 is rotated within the bore 65 by the crank member 53, the rack 57 and the surgical retractor 54 are drawn up and down through the slot 62 along the drawing axis 69, as shown in FIGS. 5 and 6. In the preferred embodiment, the pinion 56 includes two shafts 58 that are eccentric with respect to the pinion's axis of rotation 110 and preferably disposed symmetrically thereabout. The teeth 55 preferably extend laterally in a direction substantially normal to the drawing axis 69. In this configuration, the two shafts 58 alternatingly associate with the teeth 55 of the rack 57 as the pinion 56 is rotated to draw the retractor 54 through the slot 62.

The pinion 56 is preferably rotatable to a blocking position in which preferably at least the distally located shaft 58 of the pinion 56 is disposed directly under the pinion axis 110 in a direction in parallel with the drawing axis 69, and more preferably with both shafts 58 aligned parallel with the drawing axis 69, with one shaft 58 positioned at a proximal side 66 of the rack 57 and the other shaft 58 positioned at a distal side 67 of the rack 57, as shown in FIG. 6. In the blocking position, the surgical retractor 54 is preferably locked and the pinion 56 preferably blocks movement or extension of the retractor 54 through the slot 62 along the drawing axis 69. Preferably, teeth 55 extend to and slightly beyond proximal and distal sides 66,67 of the pinion 56 measured from the most proximal and distal positions in which the pinion can be positioned. Advantageously, this configuration keeps the most distal shaft 58 in the blocking position when the retractor 54 is under tension along the drawing axis 69. The surgical retractor 54 can move through the slot 62 only upon further rotation of the pinion 56 by crank member 53. The surgical retractor 54 can thus be incrementally retracted through the slot 62 in a controlled manner and the pinion 56 can be rotated to a blocking position to lock and maintain the retractor 54 in such a position.

In other embodiments, the drawing mechanism can have other configurations to enable the drawing mechanism to draw the surgical retractor through the slot along the drawing axis. In one embodiment, for example, the drawing mechanism includes a ratchet mechanism. In the preferred embodiment, as shown in FIGS. 2-4, the attachment portion is configured to hold and affix the second surgical tool support in a first plane with respect to the base portion, and the slot 62 in the drawing housing 60 that receives and guides the surgical retractor 54 is oriented to draw the surgical retractor 54 along a second plane, which is shown between the clamping member bore 34 and the first plane, to avoid interference of the surgical retractor with the post 80 or other portions of the attachment portion 70 or second surgical tool support affixed thereto. Also, the slot 62 and the attachment portion 70 as shown in are in fixed association with the base portion 30 so that the slot 62 is out of alignment from the post 80 to avoid interference with the surgical retractor 54.

Referring to FIGS. 1, 3, 4, and 8, the surgical retractor 54 is preferably configured and dimensioned for retracting the ribcage or other parts of the patient, and more preferably for retracting the xiphoid. Preferably, the surgical retractor 54 includes a rack 57, a drawing member 59, and retraction blade 94 that is attached to the end of the retractor 54 that extends below the tool holder 20. The retraction blade 94 is preferably rotatably associable with the drawing member 59 about an axis 97, and in the preferred embodiment, the blade 94 is rotatably attached by inserting a pivot pin 96, preferably a rivet, through a bore 93 of the drawing member 59 to rotatably secure the blade 94 thereto. In other embodiments, the blade can be rotatably secured to the retractor using other mechanisms and configurations, and can be fixed thereto, for example.

Figure 8:
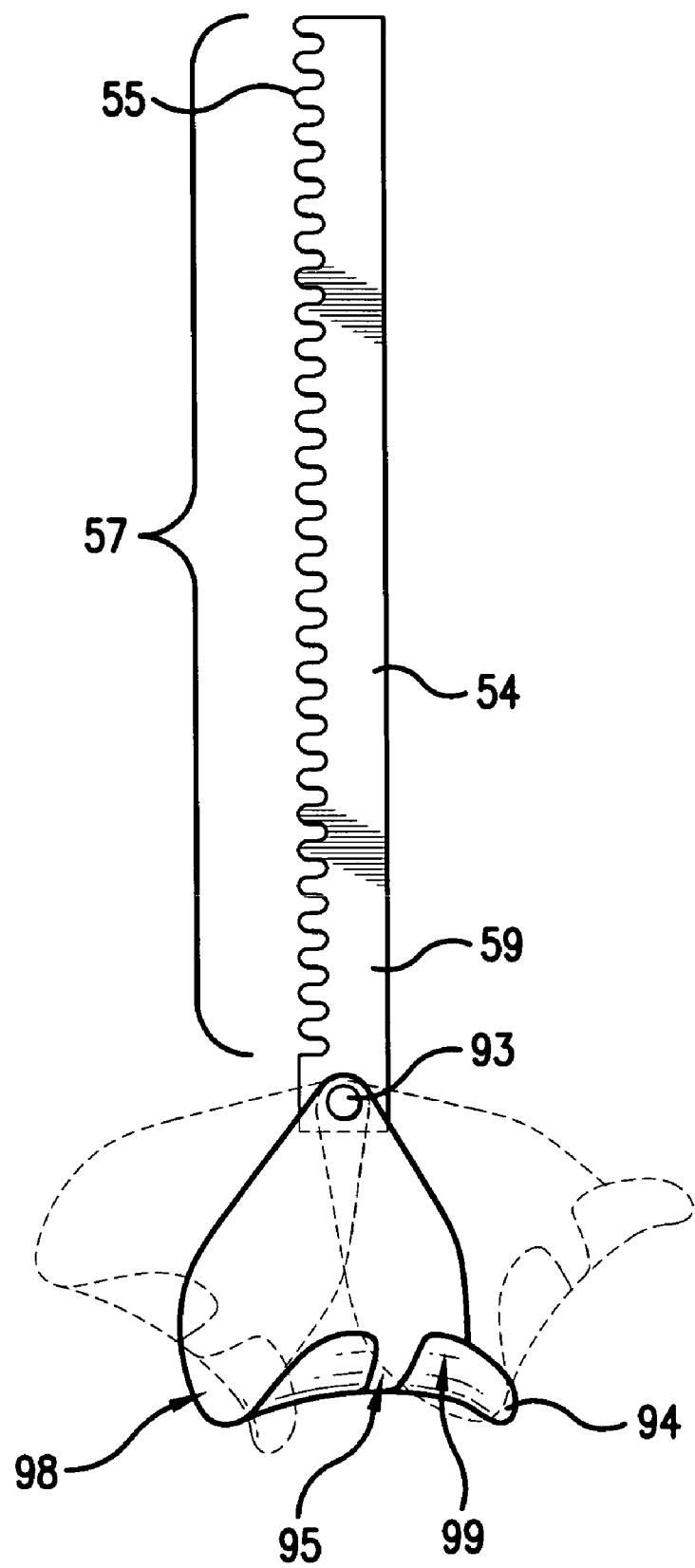
FIG. 8 is a rear view of an embodiment of a surgical retractor.

Referring to FIG. 8, the blade 94 is preferably configured and dimensioned for supportively associating with the natural curvature and dimensions of a patient's xiphoid. Preferably, the blade 94 has smooth surfaces including a concave portion 98 that faces proximally and is configured to receive a central portion of the sternum. The blade 94 preferably has a substantially saddle shape that includes a saddle point defined in the center of the bottom surface of the blade 94. More preferably, the portion of the blade that runs from the saddle point to the lateral edges thereof has a convex shape, and the portion of the blade that runs from the saddle point in the anterior-posterior direction has a concave shape. The blade is preferably more sharply flared toward the lateral edges. In alternative embodiments, the blade 94 can be dull and blunt.

The lip 99 of the blade 94, which is overall convex, can be positioned behind the xiphoid to support to the xiphoid when retracted. Different embodiments of the retraction blade include different sizes such that different blades can be used for patients having different sized xiphoids. The preferred blade 94 includes a notch or recess 95 at the bottom thereof, which is dimensioned and configured to receive a protruding tip of the xiphoid therethrough. In one embodiment, the notch 95 is preferably open at the free edge of the lip 99 and extends around the distal supporting surface. In another embodiment, the notch 95 extends to the bottom portion of the blade 94, and in another embodiment, the notch 95 extends to the front of the blade 94. Preferably, the notch 95 is aligned along the center of the blade, is generally straight, and has a width to receive the tip of a xiphoid. This configuration advantageously allows the retraction blade 94 to be positioned under the xiphoid to fully support and retract the xiphoid in the retracted position without breaking or otherwise damaging the xiphoid tip. In alternative embodiments, the retractor 54 does not have a notch and supports the entire xiphoid, or is wide enough to support both sides of the ribcage without also supporting the xiphoid.

Figure 9:
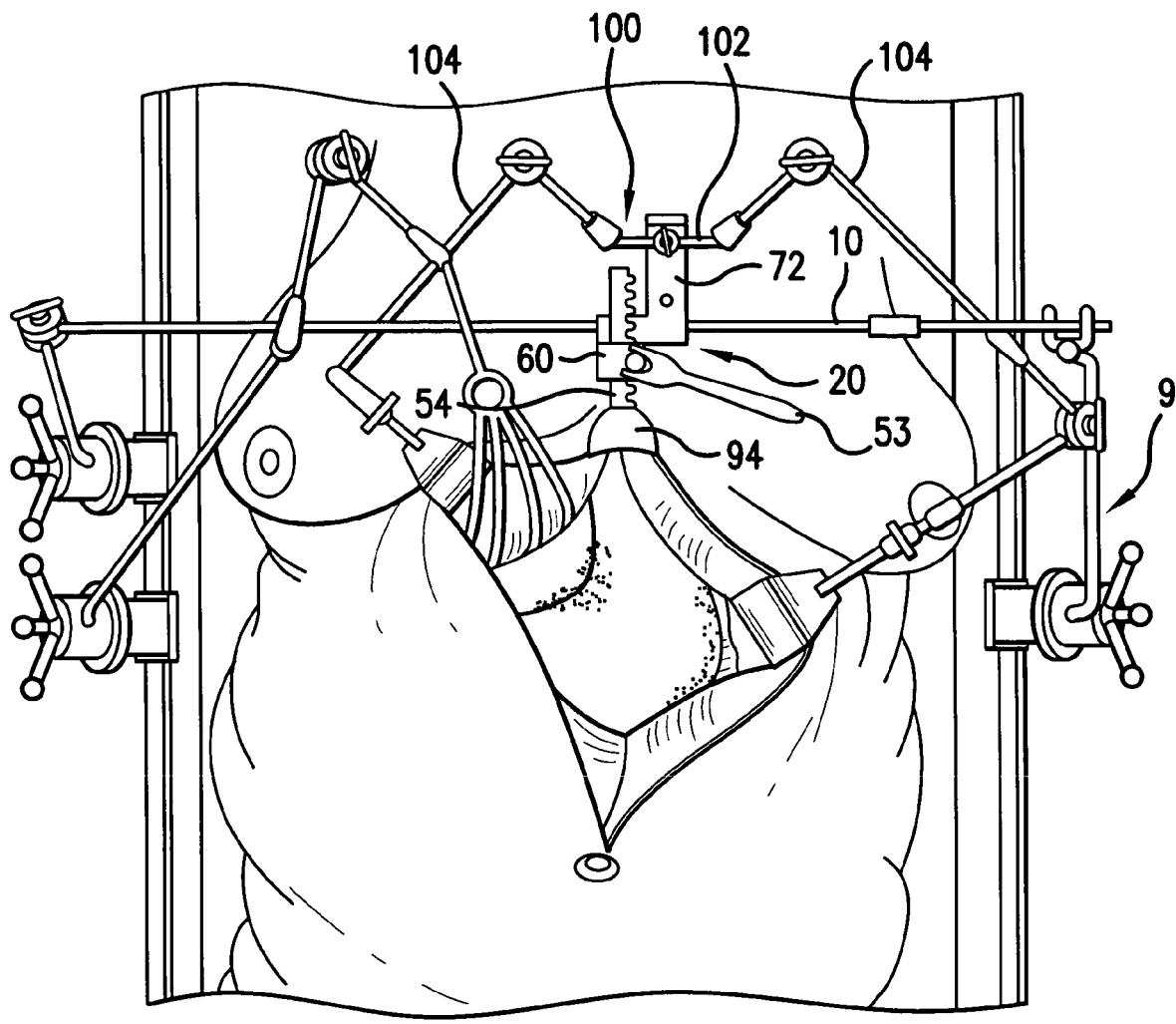
FIG. 9 is a perspective view of an embodiment of an assembly using the tool holder of FIG. 1.

In a preferred embodiment, the tool holder 20 is mounted to the cylindrical bar 10 substantially over the center of the patient's body, as shown in FIG. 9, so that the retraction blade 94 of the xiphoid retractor 54 is in an optimum position for gripping under the patient's xiphoid and supportively retracting the xiphoid upwardly to the retracted position. Advantageously, the adjustably locking feature of the association between the blade 94 and retractor 54 allows the physician to better position and lock the blade 94 under the xiphoid such that the blade 94 can fully grip and support the xiphoid in the retracted position.

The attachment portion 70 is preferably dimensioned and configured for mounting or attaching a surgical tool support to the tool holder 20, and more preferably for mounting a surgical tool support that can hold and support additional surgical tools and retractors. Referring to FIGS. 1-3, the attachment portion 70 preferably includes a post 80, which is configured for rotatably mounting a yoke 102 of a surgical tool support 100, and a securing member 90 that is operably associated with the post 80 for separably and releasably fixing the surgical tool support 100 thereto.

Referring to 3, 9 and 10, the yoke 102 preferably includes a central bore configured and dimensioned for receiving the post 80 for mounting or attaching the yoke 102 thereto. Preferably, yoke 102 is pivotably mounted to post 80 before locking thereto. The yoke 102 also preferably includes at least fixed two arms extending preferably in different directions from the bore that are configured and dimensioned for supporting other extension arms or surgical tools. In FIGS. 9 and 10, the ends of the fixed arms preferably include ball and socket members, with articulated arms 104 as known in the art extending therefrom that can be locked in various fixed positions.

The attachment portion 70 also preferably includes a platform 72 that connects the post 80, preferably supportively, to the base portion 30. Preferably, the platform 72 extends upwardly on the front side of the base portion 30 and more preferably extends from the second clamping portion 37. In the preferred embodiment, the platform 72 is of unitary construction with the second clamping portion 37. Preferably, the platform 72 is substantially flat and the post 80 extends therefrom substantially tangentially to the bore axis 35. More preferably, the post 80 extends at end of the platform 72 that is opposite the base portion 30. Preferably, the platform 72 extends from the base portion 30 at a sufficient length 73 such that manipulation of the surgical tool support 100 that is mounted on the post 80 does not interfere with manipulation of the surgical retractor 54 that is drawn by the drawing mechanism 52. In other embodiments, the platform can extend from the base portion at an angle with respect to the retraction portion 50 about the bore axis 35 that is preferably at most 90° and more preferably at most 45°.

Preferably, the incremental retraction portion 50 and the attachment portion 70 are disposed on substantially opposite ends or sides of the bore axis 35. In other embodiments, the relative positions of the incremental retraction portion and the attachment portion with respect to the bore axis can be different. Preferably, incremental retraction portion 50 and drawing axis 69 are offset from the attachment portion 70 and post 80 in the direction of the axis 35 such that manipulation of surgical tools attached to the attachment portion does not interfere with the drawing of surgical tools by the retraction portion 50. More preferably, the extension of slot 62 over which the retractor 54 will travel upon drawing the retractor therethrough is offset in the direction of the axis 35 from the post 80 of the attachment portion 70. In the preferred embodiment shown in FIG. 10, the platform 72 is offset in the direction of the axis 35 with respect to the housing 60. Additionally, the first clamping portion 36 and the key 40 received therein are preferably aligned with the platform 72 and offset in the direction of the axis 35 with respect to the housing 60 and the retractor 54 that is drawn therethrough.

The length 73 of the platform 72 is also short enough to maintain a stable and supportive connection between the post 80 and the base portion 30. Preferably, the length 73 of the platform 72 is at least about 30 mm and more preferably is at least about 50 mm. Preferably, the length 73 of the platform 72 is at most about 90 mm and more preferably is at most about 70 mm. In the preferred embodiment, the length 73 is about 60 mm.

The post 80 is preferably fixedly disposed on the platform 72, preferably by welding or adhering, such that the post 80 cannot be removed from the tool holder 20. In the preferred embodiment, the post 80 includes an extension 82 that is configured and dimensioned for fixedly associating with a bore 74 of the platform 72 such that the post 80 extends substantially orthogonally with respect to the platform 72 along a post axis 89. The post axis 89 is oriented with respect to the drawing axis 69 at an angle that is preferably at least about 45° and more preferably is at least about 60° or 80°, and preferably is at most about 135° and more preferably is at most about 120° or 100°. In the preferred embodiment, the post axis 89 and the drawing axis 69 are substantially orthogonal to each other.

The post 80 preferably has a length 81 along the post axis 89 is at least about 30 mm and more preferably is at least about 40 mm. Preferably, the length 81 is also at most about 70 mm and more preferably is at most about 60 mm. In the preferred embodiment shown in FIG. 3, the length 81 of the post 80 is about 45 mm.

Preferably, the attachment portion 70 also includes a protrusion 84 disposed for positioning the yoke 102 of the surgical tool support 100 axially on the post 80. The protrusion 84 preferably is configured and dimensioned such that yoke 102 of the surgical tool support 100 mounted on the post 80 is positioned away from the platform 72 and base portion 30 extending therefrom so as to not interfere with the surgical retractor 54 as it is drawn through the drawing mechanism 52. More preferably, there are two protrusions 84 disposed on either side of the post 80 that are configured and dimensioned for associating with the yoke 102 such that the yoke 102 can be rotatably mounted about the post 80. With the yoke 102 mounted on the post 80, the securing member 90 is preferably configured to clamp the yoke 102 against to the protrusions 84.

The post 80 preferably includes a threaded portion 86 that is configured and dimensioned for associating with the securing member 90, which is also configured for threaded association with the threaded portion 86. More preferably, the securing member 90 can screw onto the threaded portion 86 such that the securing member 90 clamps and secures the yoke 102 on the post 80. In the preferred embodiment shown in FIG. 3, the securing member 90 is configured as a wing nut 91 that includes a washer 92, which is rotatably fixed thereto. In such a configuration and as the wing nut 91 screws onto the threaded portion 86, the washer 92 pushes against the yoke 102 that is mounted on the post 80 to secure the yoke thereon. In other embodiments, the securing member 90 can have other configurations to enable it to operably associate with the post 80 to separably and releasably fix or lock the yoke 102 of a surgical tool support 102.

Referring to the embodiment shown in FIG. 9, the surgical tool support 100 is preferably dimensioned and configured to hold or attach to surgical tools such that the tools are supported and maintained in a substantially fixed and stable position. In other embodiments, the surgical tools can directly mount, clamp, or otherwise attach to the surgical tool support 100. Preferably, the surgical tools are retractors, such as for example ribcage or internal organ retractors. More preferably, the surgical tool support 100 includes independently lockable extension arms 104 that extend from the yoke 102 such that the surgical tool support 100 can maintain and support multiple surgical tools in a substantially fixed and stable position. In the preferred embodiment, the surgical tool support 100 is a hydra that has at least two or more extension arms for maintaining organ or ribcage retractors in the retracted position. The extension arms 104 of the hydra tool support advantageously allow the retractors to be easily supported and positioned from the both sides of the patient's body to retract organs or musculoskeletal structures thereto, preferably when the tool holder 20 is mounted to the cylindrical bar 10 substantially over the center of the patient's body to align the surgical retractor 54 with xiphoid for retraction thereof.

FIG. 10 shows a preferred embodiment of the tool holder 20 that includes a surgical retractor 54 in drawn association with the drawing mechanism 52. Attached to the surgical retractor 54 is a blade 94 that is configured and dimensioned for retracting a xiphoid and also includes an optical fiber 103 for positioning within the abdominal cavity. Mounted to the post of the platform 72 is a hydra tool support 100 that has two independently lockable extension arms 104 extending from ends of the yoke 102. The extension arms 104 each include a tightening joint 105 that is configured and dimensioned for simultaneously locking the various portions of the arm in a fixed position. The ends 106 of the extension arms 104 are preferably configured and dimensioned to hold and support surgical tools, such as organ and ribcage retractors. In other embodiments, the ends 106 can have universal joints, such as a ball and socket connection, for rotatably mounting surgical tools thereto.

The tool support 20 is clamped to the cylindrical bar 10, which is preferably a two-piece horizontal bar as known in the art. The tool support 20 is preferably clamped over the connection of the two pieces, substantially in the center of the bar 10. Mounted in this position, the xiphoid retractor 54 is aligned substantially with the center of the patient's body to provide easy retraction of the xiphoid.

Also clamped to either side of the cylindrical bar 10 are two platforms 4 that each include a drawing mechanism 7 and housing 5 adjustably mounted thereto. The drawing mechanisms 7 can include a rack and pinion or ratchet mechanism that can operate similar to drawing mechanism 52 previously described and shown in FIGS. 5-7 for incrementally drawing retractors 9. The housings 5 are preferably adjustably mounted to the platforms 4 such that the retractors 9 can be positioned and extended at various angles with respect to the platforms 4, but can be fixed thereto. Attached to the ends of the retractors 9 are ribcage blades 6 that are configured and dimensioned for associating with and retracting a patient's ribcage.

The cylindrical bar 10 is attached to two surgical tool supports 8, preferably as disclosed in U.S. Pat. No. 4,143,652, that extend horizontally and downwardly therefrom. Preferably, the tool supports 8 are fixedly secured to rails 3 disposed on either side of the operating table 1 by swinger clamps 2 as known in the art, for example as disclosed in U.S. Pat. No. 6,315,260. In this configuration, the tool support 20 stably and securely maintains the cylindrical bars 10 and any other equipment attached thereto in a fixed position.

The term "about," as used herein, should generally be understood to refer to both the corresponding number and a range of numbers. Moreover, all numerical ranges herein should be understood to include each whole integer within the range.

While illustrative embodiments of the invention are disclosed herein, it will be appreciated that numerous modifications and other embodiments can be devised by those of ordinary skill in the art. Features of the embodiments described herein can be combined, separated, interchanged, and/or rearranged to generate other embodiments. Therefore, it will be understood that the appended claims are intended to cover all such modifications and embodiments that come within the spirit and scope of the present invention.

What is claimed is:

1. A surgical tool holder, comprising: a clamping member that comprises a clamping part defining a bore having a bore axis in a first plane and configured for receiving and clamping to a support bar; a base portion supported from the clamping member and configured for releasably mounting to a first surgical tool support in a fixed association; an incremental retraction portion supported from the base portion and comprising: a drawing mechanism configured to operably engage and incrementally draw a surgical retractor under tension, along a drawing axis that is substantially perpendicular to the bore axis and is in a second plane to avoid interference of the surgical retractor with the support bar, to a selected position and hold the surgical retractor in the selected position, and a manually operable crank member configured to operate the drawing mechanism; and an attachment portion supported from the base portion and comprising: a post having a post axis and configured to rotatably mount a yoke of a second surgical tool support in a third plane to avoid interference of the second surgical tool support with the surgical retractor and the support bar, wherein the post axis extends in a direction substantially perpendicular to both the bore and drawing axes, and a securing member operably associated with the post to releasably fix the second surgical tool support thereto, wherein the retraction portion and the attachment portion are attached to the base portion on opposite sides of the bore axis in a substantially non-adjustable relation to each other.

2. The surgical tool holder of claim 1, wherein the base portion is configured to releasably mount to a cylindrical bar of the first surgical tool support.

3. The surgical tool holder of claim 1, wherein the attachment portion comprises a platform supportively connecting the post to the base portion, and the post extends from the platform substantially tangentially to the bore axis.

4. The surgical tool holder of claim 1, wherein the incremental retraction portion comprises a drawing housing configured to receive and guide the surgical retractor during retraction, and at least a portion of the clamping member is of unitary construction with at least a portion of the drawing housing.

5. The surgical tool holder of claim 1, wherein the attachment portion comprises a locating protrusion disposed for positioning the yoke axially on the post, wherein the securing member is operably associated with the post to clamp the post-mounted yoke against the locating protrusion, and the protrusion is disposed with respect to the retraction portion to support the second surgical tool support out of plane with the surgical retractor to avoid interference of the surgical retractor with the second surgical tool support affixed to the attachment portion.

6. The surgical tool holder of claim 5, wherein the securing member is in threaded association with the post to clamp against the yoke mounted thereon.

7. The surgical tool holder of claim 6, wherein the securing member comprises a wing nut.

8. The, surgical tool holder of claim 1, wherein the drawing mechanism and crank member are rotatable to incrementally draw the surgical retractor.

9. The surgical tool holder of claim 8, wherein the drawing mechanism comprises a pinion operably engageable with a rack of the surgical retractor.

10. A surgical retraction assembly, comprising:
the surgical tool holder of claim 9, and
a surgical retractor, which comprises a rack configured and dimensioned to mesh with the pinion to draw the rack upon rotation of the pinion.

11. The surgical retraction assembly of claim 10, wherein the rack and pinion are configured such that the pinion is rotatable to at least one blocking position in which the pinion blocks further extension of the rack from the selected position.

12. The surgical retraction assembly of claim 11, wherein the pinion is configured to draw the rack in a drawing axis and has proximal and distal sides aligned parallel to the drawing axis, the rack comprising teeth engaged with the pinion, which teeth extend to the proximal and distal sides to provide the at least one blocking position.

13. The surgical tool holder of claim 1, wherein the drawing mechanism comprises a ratchet.

14. The surgical tool holder of claim 1, wherein the bore has a bore diameter, and the incremental retraction portion is oriented to draw the surgical retractor aligned within one bore diameter outside the bore.

15. The surgical tool holder of claim 1, wherein the incremental retraction portion is oriented to draw the surgical retractor within half of one bore diameter outside the bore.

16. A surgical retraction assembly, comprising:
the surgical tool holder of claim 1;
a first surgical tool support to which the base portion is fixed;
a surgical retractor in drawn association with the incremental retraction portion; and
a second surgical tool support, which comprises a hydra, fixed on the post,
wherein the planar separation between the second surgical tool support and the incremental retraction is substantially nonadjustable, thereby preventing interference between the incremental retraction portion and the second surgical tool support.

17. The surgical retraction assembly of claim 16, wherein the surgical tool holder is positioned to, and the surgical retractor is configured to, retract a xiphoid.

18. The surgical tool holder of claim 1, wherein the incremental retraction portion comprises a drawing housing defining a slot configured and oriented to receive and guide the surgical retractor, wherein the incremental retraction portion and the attachment portion are associated with the base portion so the opening of the drawing housing is out of alignment from the post for guiding the surgical retractor to avoid interference of the surgical retractor with the second surgical tool support affixed to the attachment portion.

19. The surgical tool holder of claim 1, wherein the clamping member is configured to clamp to the support bar at a non-adjustable angle between the drawing axis and the bore axis.

20. The surgical tool holder of claim 19, wherein clamping member has a bore wall defining the bore configured to receive the support bar and enclosing the bore sufficiently on all lateral sides thereof to fix the angle between the drawing axis and a longitudinal axis of the bar.

21. The surgical retraction assembly of claim 19, wherein the surgical retractor comprises a retraction blade having a notch configured and disposed to receive the tip of a xiphoid to minimize or prevent damage thereto during the retraction thereof, and the incremental retraction portion comprises a drawing housing defining a slot that is orientated for guiding and drawing the surgical retractor along the drawing axis.

22. A method of preparing a surgical tool holder which comprises providing: a clamping member that comprises a clamping part defining a bore having a bore axis in a first plane and configured for receiving and clamping to a support bar; a base portion configured for being supported from the clamping member and that releasably mounts to a first surgical tool support in a fixed association therewith; an incremental retraction portion configured for being supported from the base portion and comprising: a drawing mechanism configured to operably engage and incrementally draw a surgical retractor under tension, along a drawing axis that is substantially perpendicular to the bore axis and is in a second plane to avoid interference of the surgical retractor with the support bar, to a selected position and hold the surgical retractor in the selected position, and a manually operable crank member configured to operate the drawing mechanism; and an attachment portion configured for being supported from the base portion and comprising; a post having a post axis and configured to rotatably mount a yoke of a second surgical tool support in a third plane to avoid interference of the second surgical tool support with the surgical retractor and the support bar, wherein the post axis extends in a direction substantially perpendicular to both the bore and drawing axes; and operatively associating a securing member with the post that releasably fixes the second surgical tool support thereto, wherein the retraction portion and the attachment portion are attached to the base portion on opposite sides of the bore axis in a substantially non-adjustable relation to each other.

* * * * *